United States Patent [19]
Levin et al.

[11] Patent Number: 6,162,814
[45] Date of Patent: Dec. 19, 2000

[54] PREPARATION AND USE OF ORTHO-SULFONAMIDO HETEROARYL HYDROXAMIC ACIDS AS MATRIX METALOPROTEINASE AND TACE INHIBITORS

[75] Inventors: Jeremy Ian Levin, Nanuet, N.Y.; Frances Christy Nelson, Wyckoff, N.J.

[73] Assignee: American Cyanamid Company, Madison, N.J.

[21] Appl. No.: 09/330,877

[22] Filed: Jun. 11, 1999

Related U.S. Application Data

[62] Division of application No. 08/944,400, Oct. 6, 1997, Pat. No. 5,962,481.
[60] Provisional application No. 60/028,969, Oct. 16, 1996.
[51] Int. Cl.[7] .................... C07D 409/12; C07D 333/38; A61K 31/381
[52] U.S. Cl. .................... 514/336; 514/447; 546/281.1; 546/281.4; 549/68
[58] Field of Search .................... 546/281.1, 281.4; 549/68; 514/336, 447

[56] References Cited

U.S. PATENT DOCUMENTS

| | | | |
|---|---|---|---|
| 5,455,258 | 10/1995 | Macpherson et al. | 514/357 |
| 5,506,242 | 4/1996 | Macpherson et al. | 514/336 |
| 5,552,419 | 9/1996 | Macpherson et. al. | 514/357 |

FOREIGN PATENT DOCUMENTS

| | | | |
|---|---|---|---|
| 606046 | 7/1994 | European Pat. Off. | |
| 757984 | 2/1997 | European Pat. Off. | |
| 780386 | 6/1997 | European Pat. Off. | |
| 19542189 | 5/1997 | Germany . | |
| WO9535275 | 12/1995 | WIPO . | |
| WO9535276 | 12/1995 | WIPO . | |
| WO9600214 | 1/1996 | WIPO . | |
| WO9627583 | 9/1996 | WIPO . | |
| WO9633172 | 10/1996 | WIPO . | |
| WO9718194 | 5/1997 | WIPO . | |
| WO9719068 | 5/1997 | WIPO | C07D 295/08 |
| WO9720824 | 6/1997 | WIPO . | |
| WO9722587 | 6/1997 | WIPO . | |
| WO9724117 | 7/1997 | WIPO . | |
| WO9727174 | 7/1997 | WIPO . | |

OTHER PUBLICATIONS

J. Med. Chem., 40, 2525, MacPherson er al. (1997).

Primary Examiner—Mukund J. Shah
Assistant Examiner—Deepak R. Rao
Attorney, Agent, or Firm—Rebecca R. Barrett

[57] ABSTRACT

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor growth and metastasis, angiogenesis, tissue ulceration, abnormal wound healing, periodontal disease, bone disease, proteinuria, aneurysmal aortic disease, degenerative cartilage loss following traumatic joint injury, demyelinating diseases of the nervous system, graft rejection, cachexia, anorexia, inflammation, fever, insulin resistance, septic shock, congestive heart failure, inflammatory disease of the central nervous system, inflammatory bowel disease, HIV infection, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization.

The TACE and MMP inhibiting ortho-sulfonamide aryl hydroxamic acids of the present invention are represented by the formula

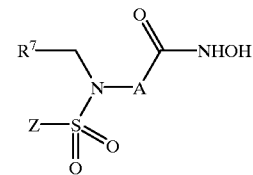

where the hydroxamic acid moiety and the sulfanamido moiety are bonded to adjacent carbons on group A where A is defined as:

a 5–6 membered heteroaryl having from 1 to 3 heteroatoms independently selected from N, O, and S and optionally substituted by $R^1$, $R^2$ and $R^3$;

and Z, $R^1$, $R^2$, $R^3$, $R^4$, $R^5$, $R^6$, $R^7$, $R^8$ and $R^9$ are described in the specification, and the pharmaceutically acceptable salts thereof and the optical isomers and diastereomers thereof.

11 Claims, No Drawings

PREPARATION AND USE OF ORTHO-SULFONAMIDO HETEROARYL HYDROXAMIC ACIDS AS MATRIX METALOPROTEINASE AND TACE INHIBITORS

This application is a divisional application of U.S. Ser. No. 08/944,400, filed Oct. 6, 1997, U.S. Pat. No. 5,962,481 which claims the benefit of prior U.S. Provisional application Ser. No. 60/028,969 filed Oct. 16, 1996.

BACKGROUND OF THE INVENTION

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor metastatis, tissue ulceration, abnormal wound healing, periodontal disease, bone disease, proteinuria, aneurysmal aortic disease, degenerative cartilage loss following traumatic joint injury, demyelinating diseases of the nervous system and HIV infection.

Matrix metalloproteinases (MMPs) are a group of enzymes that have been implicated in the pathological destruction of connective tissue and basement membranes [Woessner, J. F., Jr. *FASEB J.* 1991, 5, 2145; Birkedal-Hansen, H.; Moore, W. G. I.; Bodden, M. K.; Windsor, L. J.; Birkedal-Hansen, B.; DeCarlo, A.; Engler, J. A. *Crit. Rev. Oral Biol. Med.* 1993, 4, 197; Cawston, T. E. *Pharmacol. Ther.* 1996, 70, 163; Powell, W. C.; Matrisian, L. M. *Cur. Top. Microbiol. and Immunol.* 1996, 213, 1]. These zinc containing endopeptidases consist of several subsets of enzymes including collagenases, stromelysins and gelatinases. Of these classes, the gelatinases have been shown to be the MMPs most intimately involved with the growth and spread of tumors, while the collagenases have been associated with the pathogenesis of osteoarthritis [Howell, D. S.; Pelletier, J. -P. In *Arthritis and Allied Conditions;* McCarthy, D. J.; Koopman, W. J., Eds.; Lea and Febiger: Philadelphia, 1993; 12*th Edition* Vol. 2, pp. 1723; Dean, D. D. *Sem. Arthritis Rheum.* 1991, 20, 2; Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323].

It is known that the level of expression of gelatinase is elevated in malignancies, and that gelatinase can degrade the basement membrane which may lead to tumor metastasis [Powell, W. C.; Matrisian, L. M. *Cur. Top. Microbiol. and Immunol.* 1996, 213, 1; Crawford. H. C; Matrisian, L. M. *Invasion Metast.* 1994–95, 14, 234; Ray, J. M.; Stetler-Stevenson, W. G. *Exp. Opin. Invest. Drugs,* 1996, 5, 323; Himelstein, B. P.; Canete-Soler, R.; Bernhard, E. J.; Dilks, D. W.; Muschel, R. J. *Invasion Metast.* 1994–95, 14, 246; Nuovo, G. J.; MacConnell, P. B.; Simsir, A.; Valea, F.; French, D. L. *Cancer Res.* 1995, 55, 267–275; Walther, M. M.; Levy, A.; Hurley, K.; Venzon, D.; Linehen, W. M.; Stetler-Stevenson, W. *J. Urol.* 1995, 153 (*Suppl.* 4), 403A; Tokuraku, M; Sato, H.; Murakami, S.; Okada, Y.; Watanabe, Y.; Seiki, M. *Int. J. Cancer,* 1995, 64, 355; Himelstein, B.; Hua, J.; Bernhard, E.; Muschel, R. J. *Proc. Am. Assoc. Cancer Res. Ann. Meet.* 1996, 37, 632; Ueda, Y.; Imai, K.; Tsuchiya, H.; Fujimoto, N.; Nakanishi, I.; Katsuda, S.; Seiki, M.; Okada, Y. *Am. J. Pathol.* 1996, 148, 611; Gress, T. M.; Mueller-Pillasch, F.; Lerch, M. M.; Friess, H.; Buechler, M.; Adler, G. *Int. J. Cancer,* 1995, 62, 407; Kawashima, A.; Nakanishi, I.; Tsuchiya, H.; Roessner, A.; Obata, K.; Okada, Y. *Virchows Arch.,* 1994, 424, 547–552.]. Angiogenesis, required for the growth of solid tumors, has also recently been shown to have a gelatinase component to its pathology [Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323.]. Furthermore, there is evidence to suggest that gelatinase is involved in plaque rupture associated with atherosclerosis [Dollery, C. M.; McEwan, J. R.; Henney, A. M. *Circ. Res.* 1995, 77, 863; Zempo, N.; Koyama, N.; Kenagy, R. D.; Lea, H. J.; Clowes, A. W. *Arterioscler. Thromb. Vasc. Biol.* 1996, 16, 28; Lee, R. T.; Schoen, F. J.; Loree, H. M.; Lark, M. W., Libby, P. *Arterioscler. Thromb. Vasc. Biol.* 1996, 16, 1070.]. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

The hypothesis that MMPs are important mediators of the tissue destruction that occurs in arthritis has long been considered, since it was first recognized that these enzymes are capable of degrading collagens and proteoglycans which are the major structural components of cartilage [Sapolsky, A. I.; Keiser, H.; Howell, D. S.; Woessner, J. F., Jr.; *J. Clin. Invest.* 1976, 58, 1030; Pelletier, J. -P.; Martel-Pelletier, J.; Howell, D. S.; Ghandur-Mnaymneh, L.; Enis, J. E.; Woessner, J. F., Woessner, J. F., Jr., *Arthritis Rheum.* 1983, 26, 63.], and continues to develop as new MMPs are identified. For example, collagenase-3 (MMP-13) was cloned from breast cancer cells in 1994, and the first report that it could be involved in arthritis appeared in 1995 [Freiji, J. M.; Diez-Itza, I.; Balbin, M.; Sanchez, L. M.; Blasco, R.; Tolivia, J.; Lopez-Otin, C. *J. Biol. Chem.* 1994, 269, 16766; Flannery, C. R.; Sandy, J. D. 102-17, 41*st Ann. Meet. Orth. Res. Soc.* Orlando, Fla. Feb. 13–16, 1995.]. Evidence is accumulating that implicates MMP-13 in the pathogenesis of arthritis. A major structural component of articular cartilage, type II collagen, is the preferred substrate for MMP-13 and this enzyme is significantly more efficient at cleaving type II collagen that the other collagenases [Knauper, V.; Lopez-Otin, C.; Smith, B.; Knight, G.; Murphy, G. *J. Biol. Chem.,* 1996, 271, 1544–1550; Mitchell, P. G.; Magna, H. A.; Reeves, L. M.; Lopresti-Morrow, L. L.; Yocum, S. A.; Rosner, P. J.; Geoghegan, K. F.; Hambor, J. E. *J. Clin. Invest.* 1996, 97, 761.]. MMP-13 is produced by chondrocytes, and elevated levels of MMP-13 has been found in human osteoarthritic tissues [Reboul, P.; Pelletier, J.-P.; Hambor, J.; Magna, H.; Tardif, G.; Cloutier, J.-M.; Martel-Pelletier, J. *Arthritis Rheum.* 1995, 38 (*Suppl.* 9), S268; Shlopov, B. V.; Mainardi, C. L.; Hasty, K. A. *Arthritis Rheum.* 1995, 38 (*Suppl.* 9), S313; Reboul, P.; Pelletier, J.-P.; Tardif, G.; Cloutier, J.-M.; Martel-Pelletier, J. *J. Clin. Invest.* 1996, 7, 2011]. Potent inhibitors of MMPs were described over 10 years ago, but the poor bioavailability of these early peptidic, substrate mimetic MMP inhibitors precluded their evaluation in animal models of arthritis. More bioavailable, non-peptidic MMP inhibitors may be preferred for the treatment of diseases mediated by MMPs.

TNF-α converting enzyme catalyzes the formation of TNF-α from membrane bound TNF-α precursor protein. TNF-α is a pro-inflammatory cytokine that is now thought to have a role in rheumatoid arthritis, septic shock, graft rejection, insulin resistance and HIV infection in addition to its well documented antitumor properties. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334; *Pharmaprojects,* 1996, Therapeutic Updates 17 (Oct.), au197-M2Z.]. This observation has recently been extended to humans as well. Other conditions mediated by TNF-α are congestive heart failure, cachexia, anorexia, inflammation, fever, inflammatory disease of the central nervous system, and inflammatory bowel disease.

It is expected that small molecule inhibitors of gelatinase and TACE therefore have the potential for treating a variety of disease states. While a variety of MMP and TACE inhibitors have been identified and disclosed in the literature, the vast majority of these molecules are peptidic or peptide-like compounds that may have bioavailability and pharmacokinetic problems that would limit their clinical effectiveness. Low molecular weight, potent, long-acting, orally bioavailable inhibitors of gelatinases, collagenases and/or TACE are therefore highly desirable for the potential chronic treatment of the above mentioned disease states. Several non-peptide, sulfur-containing hydroxamic acids have recently been disclosed and are listed below.

U.S. Pat. Nos. 5,455,258, 5,506,242 and 5,552,419, as well as European patent application EP606,046A1 and WIPO international publications WO96/00214 and WO97/22587 disclose non-peptide matrix metalloproteinase inhibitors of which the compound CGS27023A is representative. The discovery of this type of MMP inhibitor is further detailed by MacPherson, et. al. in *J. Med. Chem.,* (1997), 40, 2525. Additional publications disclosing sulfonamide based MMP inhibitors which are variants of the sulfonamide-hydroxamate shown below, or the analogous sulfonamide-carboxylates, are European patent application EP-757984-A1 and WIPO international publications WO95/35275, WO95/35276, WO96/27583, WO97/19068 and WO97/27174.

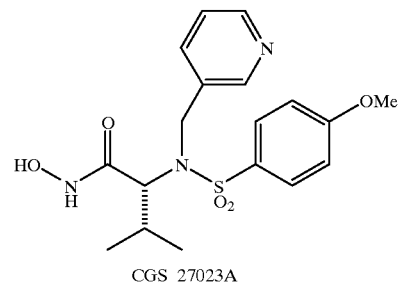

CGS 27023A

Publications disclosing β-sulfonamide-hydroxamate MMP inhibitor analogs of CGS 27023A in which the carbon alpha to the hydroxamic acid has been joined in a ring to the sulfonamide nitrogen, as shown below, include WIPO international publications WO96/33172 and WO97/20824.

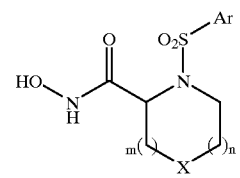

The German patent application DE19,542,189-A1 discloses additional examples of cylic sulfonamides as MMP inhibitors. In this case the sulfonamide-containing ring is fused to a phenyl ring to form an isoquinoline.

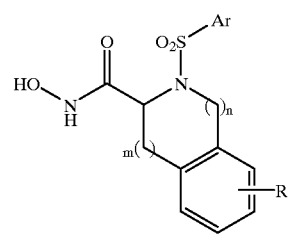

Analogs of the sulfonamide-hydroxamate MMP inhibitors in which the sulfonamide nitrogen has been replaced by a carbon atom, as shown in the general structure below, are European patent application EP-780386-A1 and WIPO international publication WO97/24117.

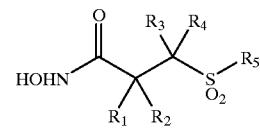

SUMMARY OF THE INVENTION

The TACE and MMP inhibiting ortho-sulfonamido heteroaryl hydroxamic acids of the present invention are represented by the formula

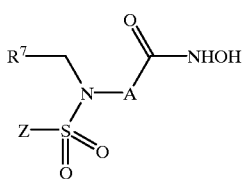

where the hydroxamic acid moiety and the sulfonamido moiety are bonded to adjacent carbons of group A where:

A is a 5–6 membered heteroaryl optionally substituted by $R^1$, $R^2$ and $R^3$; having from 1 to 3 heteroatoms independently selected from N, O, and S;

Z is aryl or heteroaryl, or heteroaryl fused to a phenyl, where aryl is phenyl, naphthyl, or phenyl fused to a heteroaryl, wherein heteroaryl is as defined above, and wherein aryl and heteroaryl may be optionally substituted by $R^1$, $R^2$, $R^3$ and $R^4$;

where heteroaryl is as defined above and optionally substituted by $R^1$, $R^2$, $R^3$ and $R^4$;

$R^1$, $R^2$, $R^3$ and $R^4$ are independently defined as —H, —$COR^5$, —F, —Br, —Cl, —I, —$C(O)NR^5OR^6$, —CN, —$OR^5$, —$C_1$–$C_4$-perfluoroalkyl, —$S(O)_xR^5$ where x is 0–2, —$OPO(OR^5)OR^6$, —$PO(OR^6)R^5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$NR^5C(=NR^6)NR^5R^6$, 3–6 membered cycloheteroalkyl having one to three heteroatoms independently selected from N, O, and S, optionally having 1 or 2 double bonds and optionally substituted by one to three groups each selected independently from $R^5$, -aryl or heteroaryl as defined above, $SO_2NHCOR^5$ or —$CONHSO_2R^5$ where $R^5$ is not H, -tetrazol-5-yl, —$SO_2NHCN$, —$SO_2NHCONR^5R^6$ or straight chain or branched —$C_1$–$C_6$ alkyl, —$C_3$–$C_6$-cycloalkyl optionally having 1 or 2 double bonds, —$C_2$–$C_6$-alkenyl, or —$C_2$–$C_6$-alkynyl each optionally substituted with —$COR^5$, —CN, —$C_2$–$C_6$ alkenyl, —$C_2$–$C_6$ alkynyl, —$OR^5$, —$C_1$–$C_4$-perfluoroalkyl, —$S(O)_xR^5$ where x is 0–2, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$C_3$–$C_6$ cycloalkyl as defined above, —$C_3$–$C_6$ cycloheteroalkyl as defined above, -aryl or heteroaryl as defined above, —$SO_2NHCOR^5$ or —$CONHSO_2R^5$ where $R^5$ is not hydrogen, —$OPO(OR^5)OR^6$, —$PO(OR^6)R^5$, -tetrazol-5-yl, —$C(O)NR^5OR^6$, —$NR^5C(=NR^6)NR^5R^6$, —$SO_2NHCONR^5R^6$ or —$SO_2NHCN$;

with the proviso that when $R^1$ and $R^2$ are on adjacent carbons of A, $R^1$ and $R^2$ together with the carbons to which they are attached can form a 5–7 membered saturated or unsaturated carbocyclic ring or heterocyclic ring containing one to two heteroatoms selected independently from N, O, and S, each optionally substituted with one to four groups selected independently from $R^4$;

$R^5$ and $R^6$ are independently defined as H, aryl and heteroaryl as defined above, —$C_3$–$C_6$-cycloalkyl as defined above, —$C_3$–$C_6$-cycloheteroalkyl as defined above, —$C_1$–$C_4$-perfluoroalkyl, or straight chain or branched —$C_1$–$C_6$ alkyl, —$C_2$–$C_6$-alkenyl, or —$C_2$–$C_6$-alkynyl each optionally substituted with —OH, —$COR^8$, —CN, —$C(O)NR^8OR^9$, —$C_2$–$C_6$-alkenyl, —$C_2$–$C_6$-alkynyl, —$OR^8$, —$C_1$–$C_4$-perfluoroalkyl, —$S(O)_xR^8$ where x is 0–2, —$OPO(OR^8)OR^9$, —$PO(OR^8)R^9$, —$OC(O)NR^8R^9$, —$COOR^8$, —$CONR^8R^9$, —$SO_3H$, —$NR^8R^9$, —$NCOR^8R^9$, —$NR^8COOR^9$, —$SO_2NR^8R^9$, —$NO_2$, —$N(R^8)SO_2R^9$, —$NR^8CONR^8R^9$, —$C_3$–$C_6$ cycloalkyl as defined above, —$C_3$–$C_6$- cycloheteroalkyl as defined above, -aryl or heteroaryl as defined above, —$SO_2NHCOR^8$ or —$CONHSO_2R^8$ where $R^8$ is not hydrogen, -ttetrazol-5-yl, —$NR^8C(=NR^9)NR^8R^9$, —$SO_2NHCONR^8R^9$, —$SO_2NHCN$;

$R^7$ is hydrogen, straight chain or branched —$C_1$–$C_6$-alkyl, —$C_2$–$C_6$-alkenyl, or —$C_2$–$C_6$-alkynyl each optionally substituted with —OH, —$COR^5$, —CN, —$C_2$–$C_6$-alkenyl, —$C_2$–$C_6$-alkynyl, —$OR^5$, —$C_1$–$C_4$perfluoroalkyl, —$S(O)_xR^5$ where x is 0–2, —$OPO(OR^5)OR^6$, —$PO(OR^5)R^6$, —$OC(O)NR^5R^6$, —$COOR^5$, —$CONR^5R^6$, —$SO_3H$, —$NR^5R^6$, —$NR^5COR^6$, —$NR^5COOR^6$, $SO_2NR^5R^6$, —$NO_2$, —$N(R^5)SO_2R^6$, —$NR^5CONR^5R^6$, —$C_3$–$C_6$ cycloalkyl as defined above, —$C_3$–$C_6$-cycloheteroalkyl as defined above, -aryl or heteroaryl as defined above, —$SO_2NHCOR^5$ or —$CONHSO_2R^5$ where $R^5$ is not hydrogen, -tetrazol-5-yl, —$NR^5C(=NR6)NR^5R^6$, —$C(O)N$ $R^5OR^6$, —$SO_2NHCONR^5R^6$ or —$SO_2NHCN$;

or $R^7$ is phenyl or naphthyl, optionally substituted by $R^1$, $R^2$, $R^3$ and $R^4$ or a 5 to 6 membered heteroaryl group having 1 to 3 heteroatoms selected independently from N, O, and S and optionally substituted by $R^1$, $R^2$, $R^3$ and $R^4$;

or $R^7$ is $C_3$–$C_6$ cycloalkyl or 3–6 membered cycloheteroalkyl as defined above;

or $R^7$ —$CH_2$—N—A—, where A is as defined above, can form a non-aromatic 1,2-heteroaryl-fused 7–10 membered heterocyclic ring optionally containing an additional heteroatom selected from O, S and N wherein said heterocyclic ring may be optionally fused to another benzene ring;

$R^8$ and $R^9$ are independently H, aryl or heteroaryl as defined above, —$C_3$–$C_7$-cycloalkyl or cycloheteroalkyl as defined above, —$C_1$–$C_4$-perfluoroalkyl, straight chain or branched —$C_1$–$C_6$-alkyl, —$C_2$–$C_6$-alkenyl, or —$C_2$–$C_6$-alkynyl, each optionally substituted with hydroxy, alkoxy, aryloxy, —$C_1$–$C_4$-perfluoroalkyl, amino, mono- and di-$C_1$–$C_6$-alkylamino, carboxylic acid, carboalkoxy and carboaryloxy, nitro, cyano, carboxamido primary, mono- and di-$C_1$–$C_6$-alkylcarbamoyl;

and the pharmaceutically acceptable salts thereof and the optical isomers and diastereomers thereof.

Preferred compounds are those wherein both of the carbons of A adjacent to the carbon bearing the sulfonamido group having a substituent other than hydrogen. Also preferred are compounds where Z is 4-alkoxyphenyl, 4-aryloxyphenyl or 4-heteroaryloxyphenyl.

The term "heteroaryl" as defined hereinabove includes, but is not limited to, pyrrole, furan, thiophene, pyridine, pyrimidine, pyridazine, pyrazine, triazole, pyrazole, imidazole, isothiazole, thiazole, isoxazole and oxazole. The term "5 to 7 membered saturated or unsaturated heterocyclic ring" includes, but is not limited to oxazolidine, thiazolidine, imidazolidine, tetrahydrofuran, tetrahydrothiophene, tetramethylene sulfone, dihydropyran, tetrahydropyran, piperidine, pyrrolidine, dioxane, morpholine, azepine and diazepine. The term "heteroaryl fused to a phenyl" includes, but is not limited to, indole, isoindole, benzofuran, benzothiophene, benzoisothiazole, quinoline, isoquinoline, quinoxaline, quinazoline, benzotriazole, indazole, benzimidazole, benzothiazole, benzisoxazole, and benzoxazole.

The following compounds (I–V) which may be used in preparing compounds of the invention are known and references are given hereinbelow. This list is included for illustrative purposes only and is not to be constituted as limiting in any way.

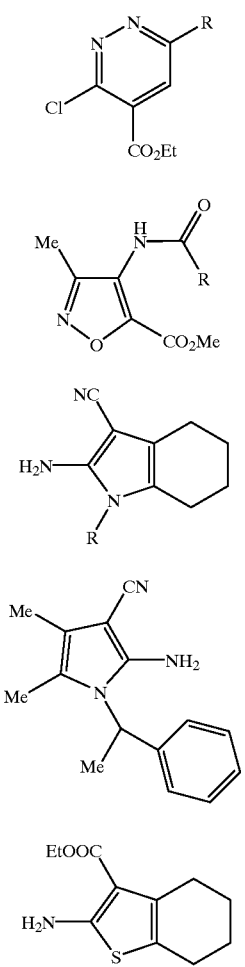

Literature references for these materials are as follows:

Compound I
  a) Dolle, R E; Hoyer, D W; Schmidt, S J; Ross, T M; Rinker, J M; Ator, M A Eur. Pat. Appl. EP-628550
  b) Wermuth, C-G; Schlewer, G; Bourguignon, J-J; Maghioros, G; Bouchet, M-J et. al. J. Med. Chem (1989), 32, 528–537
  c) Yutugi, S et. al. Chem. Pharm. Bull, (1971) 19, 2354–2364
  d) Dolle, R E; Hoyer, D; Rinker, J M; Ross, T M; Schmidt, S J Biorg. Med. Chem. Lett (1977) 7, 1003–1006

Compound II: Camparini, A; Ponticelli, F; Tedeschi, P. J. Chem. Soc., Perkin Trans. 1 (1982), 10, 2391–4.

Compound III: Muller, C. E.; Geis, U.; Grahner, B.; Lanzner, W.; Eger, K. J. Med. Chem. (1996), 39, 2482.

Compound IV: Muller, C. E.; Geis, U.; Grahner, B.; Lanzner, W.; Eger, K. J. Med. Chem. (1996), 39, 2482.

Compound V: Commercially available.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection.

DETAILED DESCRIPTION OF THE INVENTION

The following reaction scheme (Scheme I) depicts the general method of synthesis of the invention compounds from an ortho amino heteroaryl carboxylic acid ester. For purposes of illustration only, the ortho amino heteroaryl carboxylic acid ester shown is 3-amino-thiophene-4-carboxylic acid methyl ester, wherein A is thiophene, which is sulfonylated with p-methoxybenzenesulfonyl chloride, wherein Z is 4-methoxyphenyl, and then alkylated with benzyl bromide, wherein $R^7$ is benzyl. The resulting ester is subsequently converted into the corresponding hydroxamic acid in 2 steps. Obviously, other heteroaromatic groups having an amino group adjacent to a carboxy group and having optional substituents $R^1$, $R^2$ and $R^3$ where Z and $R^7$ are as defined hereinabove can be used in the general reaction scheme to prepare invention hydroxamic acids.

Scheme I

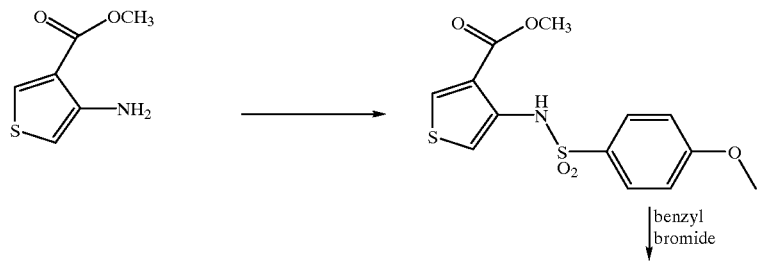

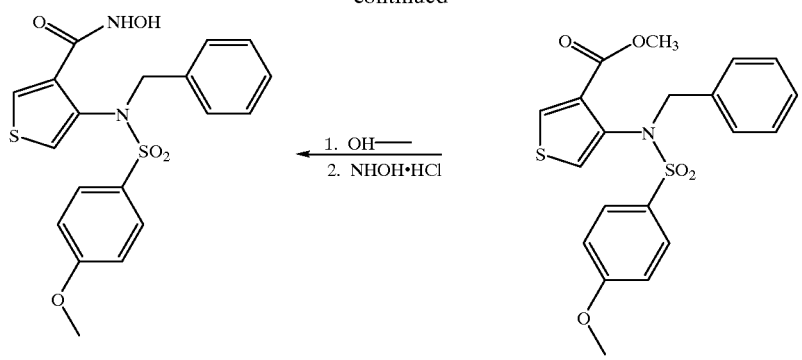

-continued

Shown in Scheme II is the synthesis of an example of the invention wherein A is pyridyl. The ortho-amino ester is constructed via metalation and subsequent carboxylation of the BOC-protected amino-pyridine. Deprotection of the resulting ester compound, (2), followed by sulfonylation of the amine, (3), provides (4) where Z is 4-methoxyphenyl. Alkylation of the NH-sulfonamide of (4) as in Scheme I, followed by hydrolysis of the ester functionality and conversion of the resulting carboxylic acid, (6), into the corresponding hydroxamic acid results in the desired pyridyl-hydroxamate, (7). Additional pyridyl-hydroxamates are available through the same route.

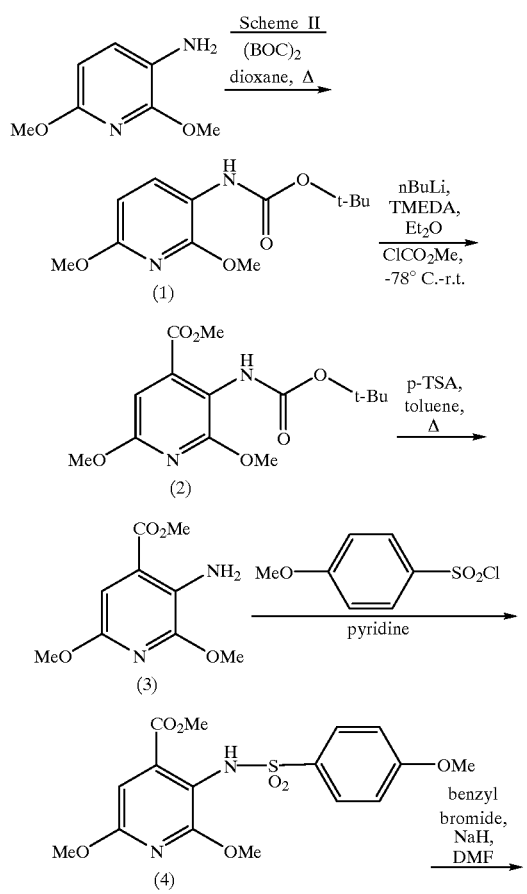

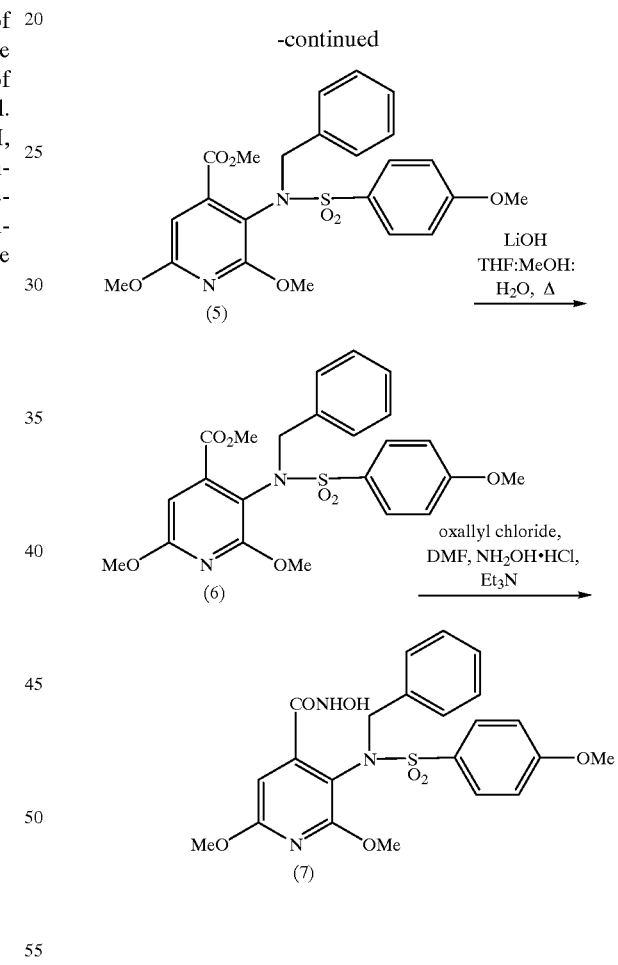

Schemes III and IV illustrate two methods for incorporating amino groups into the substituent attached to the sulfonamide nitrogen of the compounds of the invention. Thus, in Scheme III the NH-sulfonamide is alkylated with propargyl bromide to provide the propargyl sulfonamide. This alkyne is reacted with paraformaldehyde in the presence of a primary or secondary amine and cuprous chloride to give the propargyl amine which is converted, as before, to the desired hydroxamid acid.

Scheme III

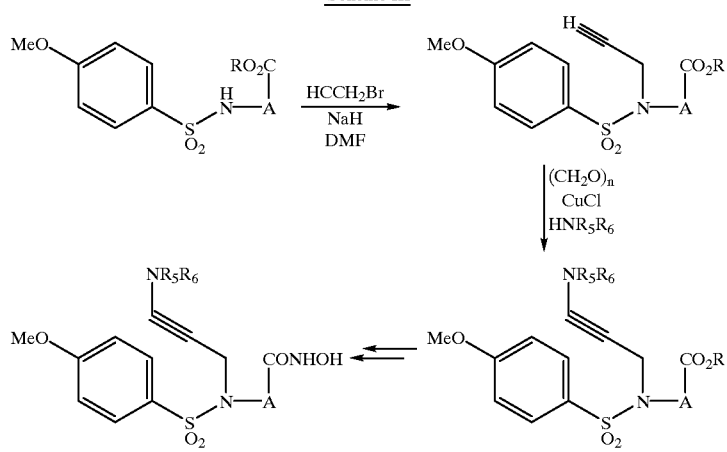

In Scheme IV, selective hydrolysis of the ester of the p-carboethoxybenzyl sulfonamide group provides a mono-carboxylic acid. This acid may be converted into an amide (not shown), followed by conversion of the second ester, A—$CO_2$R, into the corresponding hydroxamate, or reduced to the corresponding alcohol with diborane. The alcohol may be converted into the analogous amine via the benzylic bromide, followed by conversion of the ester, A—$CO_2$R, into the corresponding hydroxamate.

As shown in Scheme V, biaryl sulfonyl groups are synthesized by Suzuki couplings on a bromo-substituted benzene sulfonamide. The starting bromo-substituted benzene sulfonamide is synthesized from the commercially available bromobenzenesulfonyl chloride and the amino-acid or amino-ester, $H_2N$—A—$CO_2$R, followed by alkylation of the resulting NH-sulfonamide. Alternatively, the bromo aryl sulfonamide is converted into the corresponding boronic acid by the method of Ishiyama, et. al. [J. Org. Chem.

Scheme IV

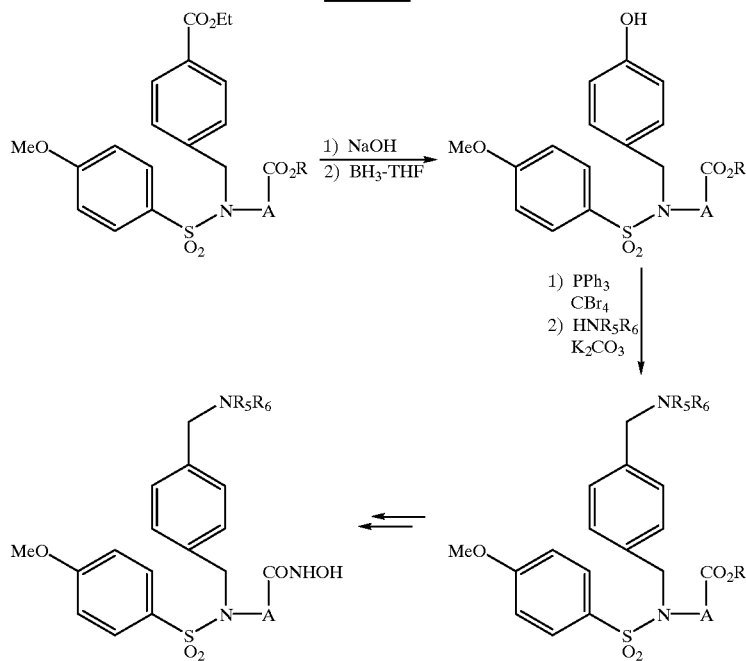

Methods for synthesizing variations of substituents on the sulfonyl aryl group are shown in Schemes V through VIII.

(1995), 60, 7508] followed by coupling with an appropriate aryl halide.

Scheme V

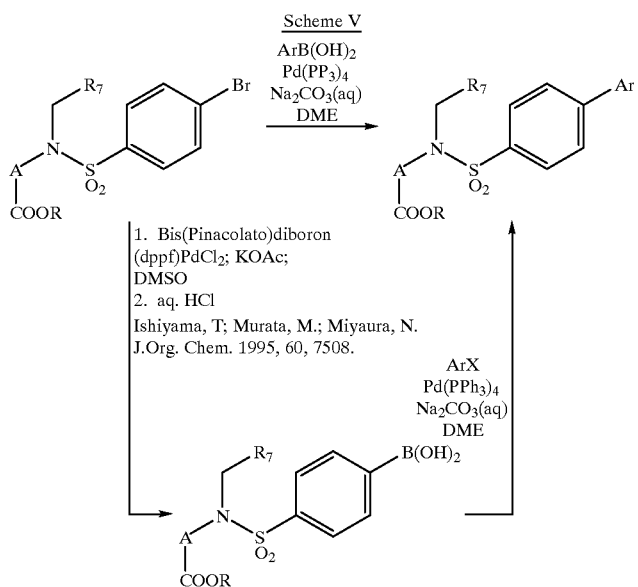

Methods for synthesizing sulfonyl aryl ethers are shown in Schemes VI through VIII. In Scheme VI biaryl ethers, or aryl heteroaryl ethers, are synthesized starting from the known sulfonyl chlorides (see for example: Zook S E; Dagnino, R; Deason, M E, Bender, S L; Melnick, M J WO 97/20824).

Scheme VI

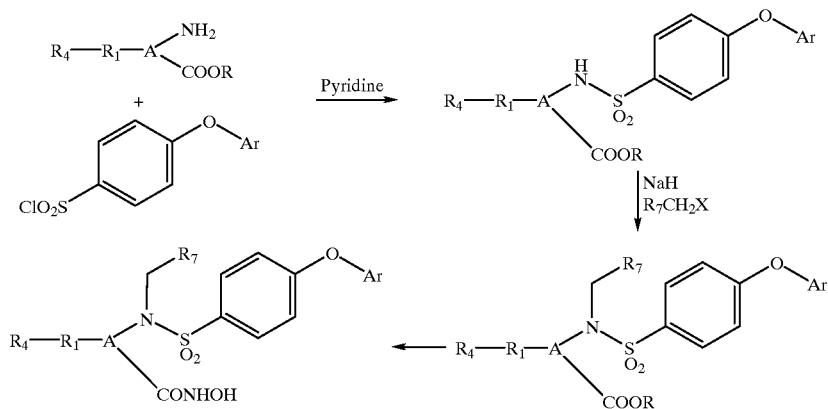

Alternatively, the biaryl ethers may be prepared from the corresponding boronic acids or via the sulfonyl phenols as shown in Scheme VII.

Scheme VII

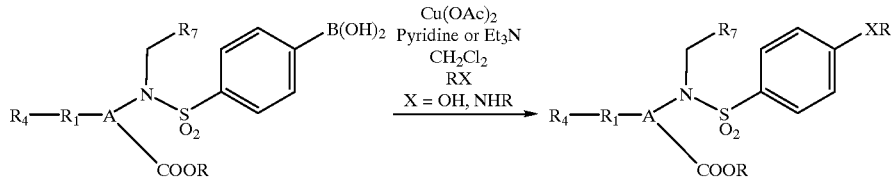

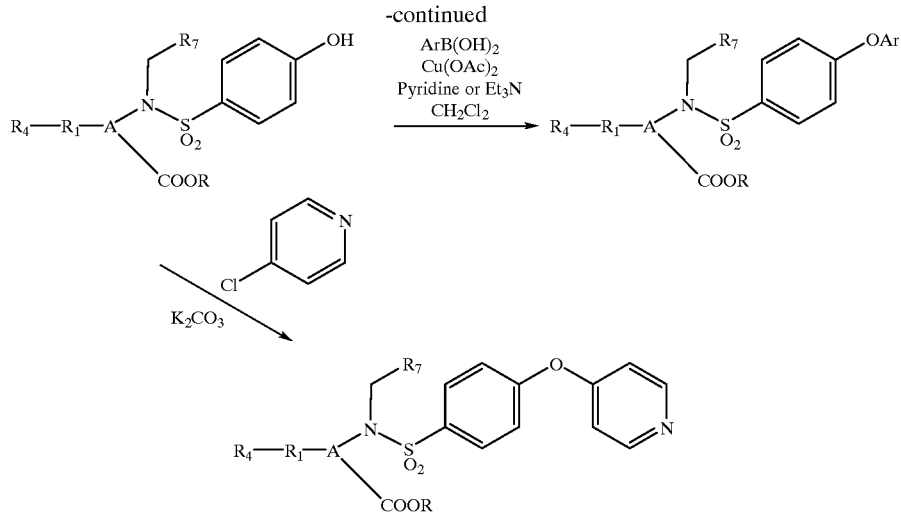

Aryl ethers may also be prepared via displacement of the fluorine from a para-fluorobenzene sulfonamide, as shown in Scheme VIII. Aryl or alkyl ethers may be prepared in this manner.

The following specific examples are included for illustrative purposes and are not to be construed as limiting to this disclosure in any way. Other procedures useful for the preparation of compounds of this invention may be apparent to those skilled in the art of organic synthesis.

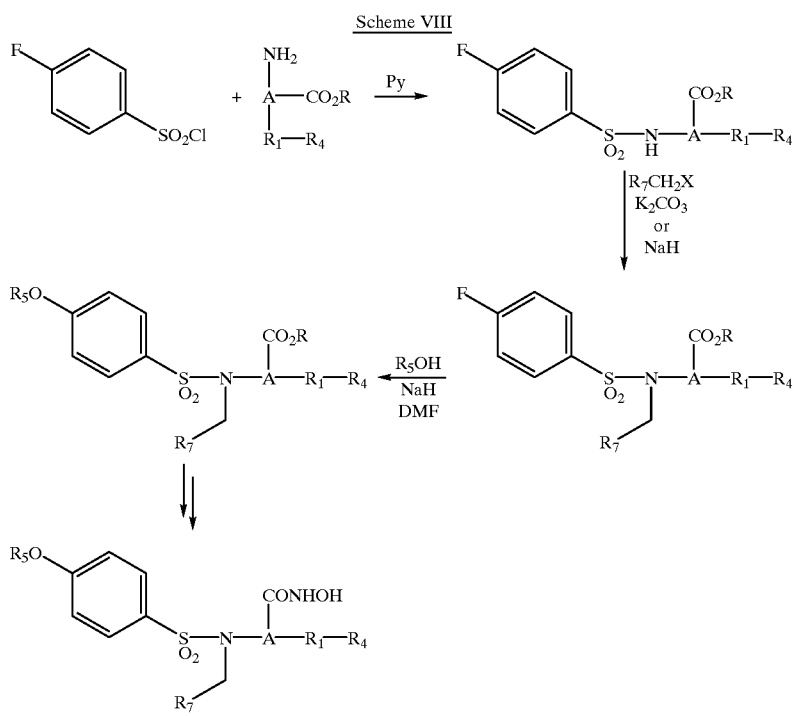

Scheme VIII

Basic salts of the hydroxamic acids can be formed with pharmaceutically acceptable alkali-forming metal cations such as lithium, sodium, potassium, calcium and aluminum. Acid addition salts can be formed when a substituent contains a basic amino group using a pharmaceutically acceptable inorganic or organic acid such as hydrochloric, hydrobromic, phosphoric, sulfuric, acetic, benzoic, succinic, lactic, malic, maleic, fumaric or methanesulfonic acids.

EXAMPLE 1

3-(4-Methoxy-benzenesulfonylamino)-thiophene-2-carboxylic acid methyl ester

To a solution of 5.00 g (0.032 mol) of 3-amino-2-carbomethoxythiophene dissolved in 40 mL of chloroform was added 7.73 mL (0.032 mol) of pyridine followed by 6.57 g (0.032 mol) of p-methoxybenzenesulfonyl chloride. The reaction mixture was stirred at room temperature for 5 h and then washed with 3N HCl and water. The organics were then dried over Na$_2$SO$_4$, filtered and concentrated in vacuo. The resulting cream colored solid was washed with ether and dried in vacuo to provide 6.89 g (66%) of the desired sulfonamide. Electrospray Mass Spec 328.2 (M+H).

EXAMPLE 2

4-(4-Methoxy-benzenesulfonylamino)-thiophene-3-carboxylic acid methyl ester

In the same manner as described in Example 1, 5.00 g (0.026 mol) of 3-amino-4-carbomethoxythiophene hydrochloride provided 3.50 g (41%) of the desired sulfonamide as a brown solid after trituration with ether. Electrospray Mass Spec 328.2 (M+H).

EXAMPLE 3

5-(4-Methoxy-benzenesulfonylamino)-1-methyl-1H-pyrazole-4-carboxylic acid ethyl ester In the same manner as described in Example 1, 2.00 g (0.012 mol) of 1-methyl-2-amino-3-carboethoxy-pyrazole provided 0.923 g (23%) of the desired sulfonamide as a white solid after recrystallization form EtOAc/Hexanes. Electrospray Mass Spec 340.2 (M+H).

EXAMPLE 4

3-(4-Methoxy-benzenesulfonylamino)-4-methyl-thiophene-2-carboxylic acid methyl ester In the same manner as described in Example 1, 4.14 g (0.024 mol) of 3-amino-4-methyl-2-carbomethoxy thiophene provided 4.89 g (47%) of the desired sulfonamide as a white solid after trituration with ether. EI Mass Spec 340.9 (M$^+$).

EXAMPLE 5

3-[Benzyl-(4-methoxy-benzenesulfonyl)-amino]-thiophene-2-carboxylic acid methyl ester To a solution of 2.0 g (6.116 mmol) of the product of Example 1 in 25 mL of DMF was added 0.257 g (6.422 mmol) of 60% sodium hydride. The resulting mixture was stirred for 30 min at room temperature and then 0.76 mL (6.422 mmol) of benzyl bromide was added. This reaction mixture was stirred overnight at room temperature, poured into water and then extracted with ether. The combined organics were washed with water and brine, dried over MgSO$_4$, filtered and concentrated in vacuo. The residue was chromatographed on silica gel eluting with EtOAc/Hexanes (1:3) to provide 1.62 g (65%) of the desired product as white crystals. CI Mass Spec: 418 (M+H).

EXAMPLE 6

4-[Benzyl-(4-methoxy-benzenesulfonyl)-amino]-thiophene-3-carboxylic acid methyl ester In the same manner as described in Example 5, 1.50 g (4.587 mmol) of the product of Example 2 provided 1.257 g (66%) of the desired product as a brown oil after chromatography on silica gel eluting with EtOAc/Hexanes (1:10). CI Mass Spec: 418 (M+H).

EXAMPLE 7

5-[Benzyl-(4-methoxy-benzenesulfonyl)-amino]-1-methyl-1H-pyrazole-4-carboxylic acid ethyl ester In the same manner as described in Example 5, 0.843 g (2.484 mmol) of the product of Example 3 provided 0.924 g (87%) of the desired product as a white solid after trituration with ether. CI Mass Spec: 430 (M+H).

EXAMPLE 8

3-[Benzyl-(4-methoxy-benzenesulfonyl)-amino]-4-methyl-thiophene-2-carboxylic acid methyl ester In the same manner as described in Example 5, 2.00 g (4.64 mmol) of the product of Example 4 provided 1.648 g (68%) of the desired product as a white solid after trituration with ether. CI Mass Spec: 432 (M+H).

EXAMPLE 9

3-[Benzyl-(4-methoxy-benzenesulfonyl)-amino]-thiophene-2-carboxylic acid

To a mixture of 1.494 g (3.583 mmol) of the product of Example 5 dissolved in 15 mL of methanol and 15 mL of THF was added 15 mL of 1N NaOH solution. The reaction mixture was stirred at room temperature for 36 h and the organics were removed in vacuo. The resulting mixture was acidified with 10% HCl and extracted with EtOAc. The combined organics were washed with water and brine, dried over MgSO$_4$, filtered and concentrated in vacuo. The resulting residue was triturated with ether and filtered to provide 1.327 g (92%) of the desired carboxylic acid as a white solid. CI Mass Spec: 404 (M+H).

EXAMPLE 10

4-[Benzyl-(4-methoxy-benzenesulfonyl)-amino]-thiophene-3-carboxylic acid

In the same manner as described in Example 9, 1.157 g (2.775 mmol) of the product of Example 6 provided 0.94 g (84%) of the desired carboxylic acid as a tan solid after trituration with ether. Electrospray Mass Spec: 404 (M+H).

EXAMPLE 11

5-[Benzyl-(4-methoxy-benzenesulfonyl)-amino]-1-methyl-1H-pyrazole-4-carboxylic acid To a solution of 0.799 g (1.862 mmol) of the product of Example 7 in 20 mL of methanol/THF (1:1) was added 9.3 mL of 1N sodium hydroxide solution and the resulting mixture was heated to reflux for 18 h. The reaction was then cooled to room temperature and the organics were removed in vacuo. The resulting mixture was acidified with 10% HCl and extracted with EtOAc. The combined organics were washed with water and brine, dried over MgSO$_4$, filtered and concentrated in vacuo. The resulting residue was triturated with ether and filtered to provide 0.697 g (93%) of the desired carboxylic acid as a white solid. Electrospray Mass Spec: 402 (M+H).

EXAMPLE 12

3-[Benzyl-(4-methoxy-benzenesulfonyl)-amino]-4-methyl-thiophene-2-carboxylic acid In the same manner as described in Example 11, 1.366 g (2.622 mmol) of the product of Example 8 provide 1.16 g (87%) of the desired carboxylic acid as a white solid after trituration with ether. Electrospray Mass Spec: 416 (M−H)—.

EXAMPLE 13

3-[Benzyl-(4-methoxy-benzenesulfonyl)-amino]-thiophene-2-carboxylic acid hydroxyamide To a solution of 0.80 g (1.985 mmol) of the product of Example 9 in 20 mL of dichloromethane was added 0.154 mL of DMF followed by 2.0 mL of 2.0M oxalyl chloride and the resulting reaction mixture was stirred at room temperature for 1 h.

In a separate flask, 1.66 mL (11.91 mmol) of triethylamine was added to a 0° C. mixture of 0.552 g (7.94 mmol) of hydroxylamine hydrochloride in 8.7 mL of THF and 2.2 mL of water. After this mixture had stirred for 15 min at 0 degrees, the acid chloride solution was added to it in one portion and the resulting solution was allowed to warm to room temperature with stirring overnight. The reaction mixture was then acidified to pH 3 with 10% HCl and extracted with EtOAc. The combined organic layers were dried over $Na_2SO_4$, filtered and concentrated in vacuo. The crude residue was triturated with ether to provide 0.66 g (80%) of the desired hydroxamic acid as a white solid. Electrospray Mass Spec: 419 (M+H).

EXAMPLE 14

4-[Benzyl-(4-methoxy-benzenesulfonyl)-amino]-thiophene-3-carboxylic acid hydroxyamide In the same manner as described in Example 13, 0.80 g (1.985 mmol) of the product of Example 10 gave 0.61 g (73%) of the desired hydroxamic acid as a white solid. Electrospray Mass Spec: 419 (M+H).

EXAMPLE 15

5-[Benzyl-(4-methoxy-benzenesulfonyl)-amino]-1-methyl-1H-pyrazole-4-carboxylic acid hydroxyamide In the same manner as described in Example 13, 0.580 g (1.446 mmol) of the product of Example 11 gave 0.446 g (74%) of the desired hydroxamic acid as a white solid. Electrospray Mass Spec: 417 (M+H).

EXAMPLE 16

3-[Benzyl-(4-methoxy-benzenesulfonyl)-amino]-4-methyl-thiophene-2-carboxylic acid hydroxyamide In the same manner as described in Example 13, 0.50 g (0.986 mmol) of the product of Example 12 gave 0.30 g (58%) of the desired hydroxamic acid as a white solid. CI Mass Spec: 433 (M+H).

EXAMPLE 17

5-Bromo-4-(4-methoxy-benzenesulfonylamino)-thiophene-3-carboxylic acid methyl ester To a solution of the product of Example 2 in 5.0 mL of $AcOH$—$CHCl_3$ (1:1) at room temperature was added 0.299 g (1.682 mmol) of N-bromosuccinimide. The reaction was stirred for 18 h and then diluted with ether, washed with water and saturated sodium bicarbonate solution, dried over $MgSO_4$, filtered and concentrated in vacuo. The tan solid residue was washed with ether-hexanes (1:1) to provide 0.504 g (81%) of the desired product as a tan solid. Electrospray Mass Spec: 406.1 (M+H)+

EXAMPLE 18

4-[Benzyl-(4-methoxy-benzenesulfonyl)-amino]-5-bromo-thiophene-3-carboxylic acid methyl ester In the same manner as described in Example 5, 0.424 g (1.044 mmol) of the product of Example 17 gave 0.400 g (77%) of the desired hydroxamic acid as a white solid. Electrospray Mass Spec: 496.1 (M+H)+

EXAMPLE 19

4-[Benzyl-(4-methoxy-benzenesulfonyl)-amino]-5-bromo-thiophene-3-carboxylic acid In the same manner as described in Example 11, 0.356 g (0.718 mmol) of the product of Example 18 gave 0.290 g (84%) of the desired hydroxamic acid as a white solid. Electrospray Mass Spec: 482.1 (M+H)+

EXAMPLE 20

4-[Benzyl-(4-methoxy-benzenesulfonyl)-amino]-5-bromo-thiophene-3-carboxylic acid hydroxyamide In the same manner as described in Example 13, 0250 g (0.519 mmol) of the product of Example 19 gave 0.222 g (86%) of the desired hydroxamic acid as a white solid. Electrospray Mass Spec: 497.1 (M+H)+

EXAMPLE 21

4-[Benzyl-(4-methoxy-benzenesulfonyl)-amino]-5-ethynyl-thiophene-3-carboxylic acid methyl ester To a solution of 0.294 g (0.634 mmol) of the product of Example 18 in 2.5 mL of DMF and 2.5 mL of triethylamine was added 0.448 mL (3.168 mmol) of trimethylsilylacetylene, 0.022 g (0.032 mmol) of bis(triphenylphosphine)-palladium(II)dichloride and 3 mg of copper(I)iodide. The reaction mixture was then heated to 80° C. for 6 h and then cooled to room temperature and diluted with ether. The organics were washed with 5% HCl solution, water and brine, dried over $MgSO_4$, filtered and concentrated in vacuo. The residue was dissolved in 5 mL of THF, 1 mL of 1M tetrabutylammonium fluoride-THF solution was added and the reaction was stirred at room temperature for 1 h, then diluted with ether, washed with 5% HCl solution, water and brine, dried over $MgSO_4$, filtered and concentrated in vacuo. The residue was chromatographed on silica eluting with EtOAc-Hex (1:5) to provide 0.159 g (61%) of the desired product as a brown oil. Electrospray Mass Spec: 442.2 (M+H)+

EXAMPLE 22

4-[Benzyl-(4-methoxy-benzenesulfonyl)-amino]-5-ethynyl-thiophene-3-carboxylic acid In the same manner as described in Example 11, 0.136 g (0.333 mmol) of the product of Example 21 provided 0.075 g (57%) of the desired product as a tan solid after chromatography on silica eluting with EtOAc-Hexanes (1:1). Electrospray Mass Spec: 428.1 (M+H)+

EXAMPLE 23

4-[Benzyl-(4-methoxy-benzenesulfonyl)-amino]-5-ethynyl-thiophene-3-carboxylic acid hydroxyamide In the same manner as described in Example 13, 0.055 g (0.634 mmol) of the product of Example 22 provided 0.044 g (77%) of the desired product as a brown foam. Electrospray Mass Spec: 443.1 (M+H)+.

EXAMPLE 24

5-Bromo-4-[(4-methoxybenzenesulfonyl)-pyridin-3-ylmethylamino]thiophene-3-carboxylic acid methyl ester To a solution of 4.80 g (11.82 mmol) of the product of Example 17 dissolved in 5.0 mL of DMF was added 2.04 g (12.41 mmol) of 3-picolyl chloride hydrochloride and 4.89 g (35.46 mmol) of potassium carbonate. The reaction mixture was then stirred at room temperature for 18 h, diluted with water and extracted with ether. The organics were then extracted with 6N HCl solution and the aqueous acid layer was then basified with 6N NaOH solution and then extracted with ether. The resulting ether layer was dried over sodium sulfate, filtered and concentrated in vacuo to provide 4.16 g (71%) of the desired product as a tan solid. Electrospray Mass Spec: 498 (M+H).

EXAMPLE 25

5-Bromo-4-[(4-methoxy-benzenesulfonyl)-pyridin-3-ylmethyl-amino]-thiophene-3-carboxylic acid To a solution of 0.40 g (0.860 mmol) of the product of Example 24 in 9.0 mL of THF-MeOH (1:1) was added 0.072 g (1.72 mmol) of lithium hydroxide monohydrate. The reaction mix was heated to reflux for 18 h and then concentrated in vacuo. The residue was was washed with THF and filtered. The filtrate was concentrated in vacuo to provide 0.388 g (100%) of the desired product as a white foam. Electrospray Mass Spec: 483 (M+H).

EXAMPLE 26

5-Bromo-4-[(4-methoxy-benzenesulfonyl)-pyridin-3-ylmethyl-amino]-thiophene-3-carboxylic acid hydroxyamide To a solution of 0.82 mL (1.63 mmol) of a 2M solution of oxalyl chloride in $CH_2Cl_2$ at 0° C. was added 0.126 mL (1.63 mmol) of DMF and the mixture was stirred at 0° C. for 15 min, then let warm to room temperature and stirred for an additional 1 h. A solution of 0.374 g (0.817 mmol) of the product of Example 193, in 1 mL of DMF, was then added to the reaction mixture and the reaction was stirred for 1 h at room temperature.

In a separate flask, 1.70 mL (12.25 mmol) of triethylamine was added to a 0° C. mixture of 0.567 g (8.165 mmol) of hydroxylamine hydrochloride in 8.1 mL of THF and 2.3 mL of water. After this mixture had stirred for 15 min at 0° C., the acid chloride solution was added to it in one portion and the resulting solution was allowed to warm to room temperature with stirring overnight. The reaction mixture next was diluted with $CH_2Cl_2$ and washed with water and saturated sodium bicarbonate solution. The organic layer was dried over $Na_2SO_4$, filtered and concentrated in vacuo. The crude residue was triturated with ether to provide 0.235 g (61%) of the desired hydroxamic acid as a tan foam. Electrospray Mass Spec: 498 (M+H).

EXAMPLE 27 tert-Butyl N-(2,6-dimethoxy-3-pyridyl)carbamate

To a suspension of 3-amino-2,6-dimethoxypyridine (1.5 g, 7.87 mol) was added di-tert-butyl dicarbonate (3.43 g, 15.7 mmol). The solution was heated at reflux for 36 hours, cooled to room temperature, and diluted with $H_2O$. The aqueous solution was extracted 3 times with EtOAc, the organic extracts were combined, washed with brine, dried over $MgSO_4$, concentrated in vacuo. The residue was purified by column chromatography using hexane/ethyl acetate as eluant (gradient 100% to 4/1) to provide 2.00 g (100%) of tert-butyl N-(2,6-dimethoxy-3-pyridyl)carbamate a yellow oil. Electrospray Mass Spec: 254.9 (M+H)+

EXAMPLE 28 tert-Butyl N-(4-carbomethoxy-2,6-dimethoxy-3-pyridyl)carbamate

The product of Example 27 (1 g, 3.93 mmol) was dissolved in $Et_2O$ (35 mL) and TMEDA (1.7 mL, 1.18 mmol) and cooled to −78° C. n-Butyllithium (4.75 mL, 11.87 mmol) was added dropwise and the reaction was allowed to stir for 15 minutes at −78° C. before warming to −10° C. for 2.5 hours. The solution was cooled back to −78° C. and methyl chloroformate (0.6 mL, 7.8 mmol) dissolved in $Et_2O$ (4.5 mL) was added dropwise. The reaction was held at −78° C. for 10 minutes and then warmed to −10° C. and allowed to stir for 1.5 hours before quenching with $NH_4Cl$(sat). The reaction mixture was extracted 3× with EtOAc. The organics were combined, washed with brine, dried over $MgSO_4$, concentrated in vacuo. The residue was purified by column chromatography using hexane/ethyl acetate as eluant (gradient 9/1 to 4/1) to provide 0.423 g (34%) of tert-butyl N-(4-carbomethoxy-2,6-dimethoxy-3-pyridyl)carbamate as a white solid. Electrospray Mass Spec: 312.8 (M+H)+

EXAMPLE 29

Methyl 3-amino-2,6-dimethoxyisonicotinate p-Toluene sulfonic acid hydrate (0.282 g, 1.48 mmol) was dissolved in toluene (11 mL) and heated to reflux overnight with azeotropic removable of $H_2O$ (Dean-Stark trap). The next day, the reaction was cooled to room temperature and the product of Example 28, dissolved in toluene (4 mL), was added. The reaction was heated back to reflux for 0.5 hours. The reaction was cooled to room temperature and poured into $NaHCO_3$ (sat) and extracted 3 times with ether. The organics were combined, washed with brine, dried over $MgSO_4$, concentrated in vacuo. The residue was purified by column chromatography using hexane/ethyl acetate as eluant (gradient 100% to 9/1) to provide 0.278 g (97%) of methyl 3-amino-2,6-dimethoxyisonicotinate as a yellow solid. Electrospray Mass Spec: 212.8 (M+H)+

EXAMPLE 30

Methyl 3-(4-methoxy-benzenesulfonylamino)-2,6-dimethoxy-isonicotinate

To a solution of the product of Example 29 (0.278 g, 1.31 mmol) in pyridine (2 mL) was added p-methoxybenzenesulfonyl chloride (0.28 g, 1.38 mmol). The reaction mixture was stirred at room temperature overnight and was then quenched with $H_2O$. The mixture was extracted 3 times with ether. The organics were combined, washed with brine, dried over $MgSO_4$, concentrated in vacuo to provide 0.444 g (89%) of methyl 3-(4-methoxy-benzenesulfonylamino)-2,6-dimethoxy-isonicotinate as a solid. Electrospray Mass Spec: 382.8 (M+H)+

EXAMPLE 31

Methyl 3-[Benzyl-(4-methoxy-benzenesulfonyl)-amino]-2,6-dimethoxy-isonicotinate

The product of Example 30 (0.444 g, 1.16 mmol) was dissolved in DMF (4 mL) and cooled to 0° C. Benzyl bromide (0.186 mL, 1.6 mmol) followed by NaH (56 mg, 1.39 mmol, 60% dispersion in mineral oil) were added and the reaction was allowed to warm to room temperature. After 1 h, the reaction was diluted with water and extracted 4× $Et_2O$. The organics were combined, washed with brine, dried over $MgSO_4$, concentrated in vacuo to provide 0.545 g (100%) of pure methyl 3-[Benzyl-(4-methoxy-benzenesulfonyl)-amino]-2,6-dimethoxy-isonicotinate as an oil. Electrospray Mass Spec: 472.9 (M+H)+

EXAMPLE 32

3-[Benzyl-(4-methoxy-benzenesulfonyl)-amino]-2,6-dimethoxy-isonicotinic acid

The product of Example 31 was hydrolyzed to the corresponding carboxylic acid using the procedure of Example 25 to provide 3-[Benzyl-(4-methoxy-benzenesulfonyl)-amino]-2,6-dimethoxy-isonicotinic acid. Electrospray Mass Spec; 459.0 (M+H)+

EXAMPLE 33

3-[Benzyl-(4-methoxy-benzenesulfonyl)-amino]-N-hydroxy-2,6-dimethoxy-isonicotinamide The carboxylic acid product of Example 32 was converted to the corresponding hydroxamic acid, 3-[benzyl-(4-methoxy-benzenesulfonyl)-amino]-N-hydroxy-2,6-dimethoxy-isonicotinamide using the procedure of Example 26. Electrospray Mass Spec: 474.0 (M+H)+

Pharmacology

Procedures for Measuring MMP-1, MMP-9, and MMP-13 Inhibition

These assays are based on the cleavage of a thiopeptide substrates such as Ac-Pro-Leu-Gly(2mercapto-4 methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with assay buffer (50 mM HEPES, pH 7.5, 5 mM $CaCl_2$, 0.02% Brij) to the desired final concentration. The assay buffer, enzyme, vehicle or inhibitor, and DTNB/substrate are added in this order to a 96 well plate (total reaction volume of 200 µl) and the increase in color is monitored spectrophotometrically for 5 minutes at 405 nm on a plate reader and the increase in color over time is plotted as a linear line.

Alternatively, a fluorescent peptide substrate is used. In this assay, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cystein), with human recombinant MMP-1, MMP-9, or MMP-13. The substrate is dissolved in methanol and stored frozen in 1 mM aliquots. For the assay, substrate and enzymes are diluted in HCBC buffer to the desired concentration. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide assays, the slope of the line is calculated and represents the reaction rate. The linearity of the reaction rate is confirmed ($r^2 > 0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

Procedure for Measuring TACE Inhibition

Using 96-well black microtiter plates, each well receives a solution composed of 10 µL TACE (Immunex, final concentration 1 µg/mL), 70 µL Tris buffer, pH 7.4 containing 10% glycerol (final concentration 10 mM), and 10 µL of test compound solution in DMSO (final concentration 1 µM, DMSO concentration <1%) and incubated for 10 minutes at room temperature. The reaction is initiated by addition of a fluorescent peptidyl substrate (final concentration 100 µM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2 > 0.85$). The mean (s±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Results of the above in-vitro matrix metalloproteinase inhibition and TACE inhibition pharmacological assays are given in Table I below.

Table I. Inhibition of MMP and TACE

| Example | MMP-1[1] | MMP-9[1] | MMP-13[1] | TACE[1] |
|---------|----------|----------|-----------|---------|
| 13 | 19.3(1) | 57.3(10) | | |
| 14 | 40(1) | 66.8(10) | | |
| 15 | 22.1(1) | 930 | | |
| 16 | | 104.1 | | |
| 20 | 638.5 | 236.4 | 471.5 | |
| 23 | 48.9(1) | 38.4(300) | 35(300) | |
| 26 | 1000 | 70 | 296 | 42%(1) |
| 33 | 1227 | 15 | 47 | 294 |

[1]$IC_{50}$ nM or % inhibition (concentration, $\mu$M)

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidin, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of rooms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. A compound having the formula:

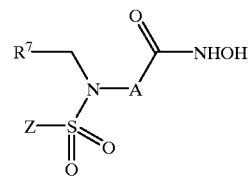

where the hydroxamic acid moiety and the sulfonamido moiety are bonded to adjacent carbons of group A where:
  A is thiophenyl optionally substituted by $R^1$, $R^2$, $R^3$ and $R^4$;
  Z is aryl or heteroaryl, or heteroaryl fused to a phenyl or another heteroaryl, where aryl is phenyl, naphthyl, or phenyl fused to a heteroaryl, wherein heteroaryl is a 5–6 membered heteroaryl group having from 1 to 3 heteroatoms independently selected from N, O, and S and, wherein this aryl and heteroaryl may be optionally substituted by $R^1$, $R^2$, $R^3$ and $R^4$;

where heteroaryl is as defined above and optionally substituted by $R^1$, $R^2$, $R^3$ and $R^4$;

$R^1$, $R^2$, $R^3$ and $R^4$ are independently defined as —H, —$COR^5$, —F, —Br, —Cl, —I, —$C(O)NR^5OR^6$, —CN, —$OR^5$, —$C_1$–$C_4$-perfluoroalkyl, —$S(O)_xR^5$ where x is 0–2, —$OPO(OR^5)OR^6$, —$PO(OR^6)R^5$, —$OC(O)NR^5R^6$, —$COOR^5$, —$CONR^5R^6$, —$SO_3H$, —$NR^5R^6$, —$NR^6COR^6$, —$NR^5COOR^6$, —$SO_2NR^5R^6$, —$NO_2$, —$N(R^5)SO_2R^6$, —$NR^5CONR^5R^6$, —$NR^5C(=NR^6)NR^5R^6$, 3–6 membered cycloheteroalkyl having one to three heteroatoms independently selected from N, O, and S, optionally having 1 or 2 double bonds and optionally substituted by one to three groups each selected independently from $R^5$, -aryl or heteroaryl as defined above, $SO_2NHCOR^5$ or —$CONHSO_2R^5$ where $R^5$ is not H, -tetrazol-5-yl, —$SO_2NHCN$, —$SO_2NHCONR^5R^6$ or straight chain or branched —$C_1$–$C_6$ alkyl, —$C_3$–$C_6$-cycloalkyl optionally having 1 or 2 double bonds, —$C_2$–$C_6$-alkenyl, or —$C_2$–$C_6$-alkynyl each optionally substituted with —$COR^5$, —CN, —$C_2$–$C_6$ alkenyl, —$C_2$–$C_6$ alkynyl, —$OR^5$, —$C_1$–$C_4$-perfluoroalkyl, —$S(O)_xR^5$ where x is 0–2, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$C_3$–$C_6$ cycloalkyl as defined above, —$C_3$–$C_6$ cycloheteroalkyl as defined above, -aryl or heteroaryl as defined above, —$SO_2NHCOR^5$ or —$CONHSO_2R^5$ where $R^5$ is not hydrogen, —$OPO(OR^5)OR^6$, —$PO(OR^6R^5$, -tetrazol-5-yl, —$C(O)NR^5OR^6$, —$NR^5C(=NR^6)NR^5R^6$, —$SO_2NHCONR^5R^6$ or —$SO_2NHCN$;

with the proviso that when $R^1$ and $R^2$ are on adjacent carbons of A, $R^1$ and $R^2$ together with the carbons to which they are attached can form a 5–7 membered saturated or unsaturated carbocyclic ring or heterocyclic ring containing one to two heteroatoms selected independently from N, O, and S, each optionally substituted with one to four groups selected independently from $R^4$;

$R^5$ and $R^6$ are independently H, aryl and heteroaryl as defined above, —$C_3$–$C_6$-cycloalkyl as defined above, —$C_3$–$C_6$-cycloheteroalkyl as defined above, —$C_1$–$C_4$-perfluoroalkyl, or straight chain or branched —$C_1$–$C_6$ alkyl, —$C_2$–$C_6$-alkenyl, or —$C_2$–$C_6$-alkynyl each optionally substituted with —OH, —$COR^8$, —CN, —$C(O)NR^8R^9$, —$C_2$–$C_6$-alkenyl, —$C_2$–$C_6$-alkynyl, —$OR^8$, —$C_1$–$C_4$-perfluoroalkyl, —$S(O)_xR^8$ where x is 0–2, —$OPO(OR^8)OR^9$, —$PO(OR^8)R^9$, —$OC(O)NR^8R^9$, —$COOR^8$, —$CONR^8R^9$, —$SO_3H$, '$NR^8R^9$, —$NCOR^8R^9$, —$NR^8COOR^9$, —$SO_2NR^8R^9$, —$NO_2$, —$N(R^8)SO_2R^9$, —$NR^8CONR^8R^9$, —$C_3$–$C_6$ cycloalkyl as defined above, —$C_3$–$C_6$- cycloheteroalkyl as defined above, -aryl or heteroaryl as defined above, —$SO_2NHCOR^8$ or —$CONHSO_2R^8$ where $R^8$ is not hydrogen, -tetrazol-5-yl, —$NR^8C(=NR^9)NR^8R^9$, —$SO_2NHCONR^8R^9$, —$SO_2NHCN$;

$R^7$ is hydrogen, straight chain or branched —$C_1$–$C_6$-alkyl, —$C_2$–$C_6$-alkenyl, or —$C_2$–$C_6$-alkynyl each optionally substituted with —OH, —$COR^5$, —CN, —$C_2$–$C_6$-alkenyl, —$C_2$–$C_6$-alkynyl, —$OR^5$, —$C_1$–$C_4$-perfluoroalkyl, —$S(O)_xR^5$ where x is 0–2, —OPO $(OR^5)OR^6$, —$PO(OR^5)R^6$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$C_3$–$C_6$ cycloalkyl as defined above, —$C_3$–$C_6$-cycloheteroalkyl as defined above, -aryl or heteroaryl as defined above, —$SO_2NHCOR^5$ or —$CONHSO_2R^5$ where $R^5$ is not hydrogen, -tetrazol-5-yl, —$NR^5C(=NR6)$, —$C(O)NR^5OR^6$, —$SO_2NHCONR^5R^6$ or —$SO_2NHCN$;

or $R^7$ is phenyl or naphthyl, optionally substituted by $R^1$, $R^2$, $R^3$ and $R^4$ or a 5 to 6 membered heteroaryl group having 1 to 3 heteroatoms selected independently from N, O, and S optionally substituted by $R^1$, $R^2$, $R^3$ and $R^4$;

or $R^7$ is $C_3$–$C_6$ cycloalkyl or 3–6 membered cycloheteroalkyl as defined above;

$R^8$ and $R^9$ are independently H, aryl or heteroaryl as defined above, —$C_3$–$C_7$-cycloalkyl or cycloheteroalkyl as defined above, —$C_1$–$C_4$-perfluoroalkyl, straight chain or branched —$C_1$–$C_6$-alkyl, —$C_2$–$C_6$-alkenyl, or —$C_2$–$C_6$-alkynyl, each optionally substituted with hydroxy, alkoxy, aryloxy, —$C_1$–$C_4$-perfluoroalkyl, amino, mono- and di-$C_1$–$C_6$-alkylamino, carboxylic acid, carboalkoxy and carboaryloxy, nitro, cyano, carboxamido primary, mono- and di-$C_1$–$C_6$-alkylcarbamoyl;

a pharmaceutically acceptable salt thereof where one may be formed;

and an optical isomer or diastereomer thereof where optical isomers and diastereomers exist.

2. A compound according to claim 1 wherein both of the carbons of A adjacent to the carbon bearing the sulfonamido group have a substituent other than hydrogen.

3. A compound according to claim 2 wherein the Z group is para-alkoxyphenyl, para-aryloxyphenyl or para-heteroaryloxyphenyl.

4. A compound according to claim 3 which is selected form the group consisting of:

3-[Benzyl-(4-methoxy-benzenesulfonyl)-amino]-4-methyl-thiophene-2-carboxylic acid hydroxyamide, 4-[Benzyl-(4-methoxy-benzenesulfonyl)-amino]-5-bromo-thiophene-3-carboxylic acid hydroxyamide, 4-[Benzyl-(4-methoxy-benzenesulfonyl)-amino]-5-ethynyl-thiophene-3-carboxylic acid hydroxyamide, and 5-bromo-4-[(4-methoxy-benzenesulfonyl)-pyridin-3-ylmethyl-amino]-thiophene-3-carboxylic acid hydroxyamide.

5. A compound according to claim 1 which is selected from the group consisting of:

3-[Benzyl-(4-methoxy-benzenesulfonyl)-amino]-thiophene-2-carboxylic acid hydroxyamide; and 4-[Benzyl-(4-methoxy-benzenesulfonyl)-amino]-thiophene-3-carboxylic acid hydroxyamide.

6. A method of inhibiting pathological changes mediated by matrix metalloproteinases in mammals which comprises administration to a mammal in need thereof a therapeutically effective amount of a matrix metalloproteinase inhibiting compound according to claim 1.

7. The method according to claim 6 wherein the condition treated is atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastatis, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating disease of the nervous system cirrhosis of the liver, glomerular disease of the kidney, premature rupture of fetal membranes, inflammatory bowel disease, or periodontal disease.

8. The method according to claim 6 wherein the condition treated is age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

9. A method of inhibiting pathological changes mediated by TNF-α converting enzyme (TACE) in mammals which comprises administration to a mammal in need thereof a therapeutically effective amount of a TACE inhibiting compound according to claim 1.

10. The method according to claim 9 wherein the condition treated is rheumatoid arthritis, graft rejection, cachexia, anorexia, inflammation, fever, insulin resistance, septic shock, congestive heart failure, inflammatory disease of the central nervous system, inflammatory bowel disease, or HIV infection.

11. A pharmaceutical composition comprising a pharmaceutical carrier and a therapeutically effective amount of a matrix metalloproteinase or TACE inhibiting compound according to claim 1.

* * * * *